(12) United States Patent
Borges et al.

(10) Patent No.: US 10,456,523 B2
(45) Date of Patent: Oct. 29, 2019

(54) MANAGEMENT OF CARE AREA TRANSITIONS OF INTRAVENOUS INFUSIONS

(71) Applicant: CareFusion 303, Inc., San Diego, CA (US)

(72) Inventors: Gregory Borges, San Diego, CA (US); Jeffrey L. Gaetano, San Diego, CA (US); Eugene Arthur Rozell, San Diego, CA (US); Stephen Bollish, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 5 days.

(21) Appl. No.: 13/830,132

(22) Filed: Mar. 14, 2013

(65) Prior Publication Data

US 2014/0278458 A1    Sep. 18, 2014

(51) Int. Cl.
*A61M 5/172*    (2006.01)
*G06F 19/00*    (2018.01)

(52) U.S. Cl.
CPC ......... *A61M 5/172* (2013.01); *G06F 19/3468* (2013.01)

(58) Field of Classification Search
None
See application file for complete search history.

(56) References Cited

U.S. PATENT DOCUMENTS 5,781,442 A * 7/1998 Engleson ............... G16H 40/20
                                                    700/214
8,185,322 B2   5/2012 Schroeder et al.
(Continued)

FOREIGN PATENT DOCUMENTS

CN    1493049 A    4/2004
CN    1748219 A    3/2006
(Continued)

OTHER PUBLICATIONS

Barnsteiner JH. Medication Reconciliation. In: Hughes RG, editor. Patient Safety and Quality: An Evidence-Based Handbook for Nurses. Rockville (MD): Agency for Healthcare Research and Quality (US); Apr. 2008 Chapter 38. Available from: http://www.ncbi.nlm.nih.gov/books/NBK2648/.*
Baxter, Colleague 3 Volumetric Infusion Pump Owners Manual—pages from dated 2000.*
Definition—"allow" as downloaded from Google on Apr. 27, 2016.*
(Continued)

*Primary Examiner* — Neal Sereboff
(74) *Attorney, Agent, or Firm* — Mintz Levin Cohn Ferris Glovsky and Popeo, P.C.

(57) ABSTRACT

An infusion device providing an in-progress infusion of at least one of a drug or a fluid consistent with one or more parameters of a first care area in a hospital can be transitioned to a second care area of the hospital. Details of the in-progress infusion can be compared against one or more second parameters defined for the second care area, and a compatibility determination can be made between the in-progress infusion and the one or more second parameters defined for the seconds care area. A handling mode of the in-progress infusion in the second care area can be selected based on the compatibility determination, and the in-progress infusion can be resolved consistent with the selected handling mode. Related apparatus, systems, techniques and articles are also described.

5 Claims, 3 Drawing Sheets

(56) References Cited

U.S. PATENT DOCUMENTS

| | | |
|---|---|---|
| 8,380,536 B2 | 2/2013 | Howard et al. |
| 2005/0144043 A1 | 6/2005 | Holland et al. |
| 2006/0026205 A1 | 2/2006 | Butterfield |
| 2006/0190302 A1* | 8/2006 | Eggers .................. G16H 40/40 705/3 |
| 2007/0033073 A1* | 2/2007 | Tajaliawal ............. G06Q 50/22 705/3 |
| 2009/0153058 A1* | 6/2009 | Feng .................... A61M 5/142 315/76 |
| 2009/0171289 A1* | 7/2009 | Davis ................ A61M 5/14212 604/131 |
| 2010/0010647 A1 | 1/2010 | Schroeder et al. |
| 2013/0204227 A1* | 8/2013 | Bochenko ........... G06F 19/3456 604/506 |
| 2013/0297330 A1* | 11/2013 | Kamen ............... G06F 19/3462 705/2 |
| 2015/0363573 A1* | 12/2015 | Schneider ........... G06F 19/3456 705/2 |

FOREIGN PATENT DOCUMENTS

| | | |
|---|---|---|
| CN | 101044487 A | 9/2007 |
| CN | 102813977 A | 12/2012 |
| EP | 2336924 A1 | 6/2011 |
| JP | 2011506048 A | 3/2011 |
| JP | 2012070991 A | 4/2012 |
| WO | WO-2009/079640 A2 | 6/2009 |

OTHER PUBLICATIONS

Anonymous. "SMART Infusion Pump Administration of Intravenous Therapy & Medications at North York General Hospital." Jan. 31, 2013. pp. 1-40. Retrieved from the Internet. [retrieved on Sep. 16, 2014].

Hughes, Ronda G., ed. Patient Safety and Quality: An Evidence-Based Handbook for Nurses. Agency for Healthcare Research and Quality, 2008. 1403 pages.

* cited by examiner

MANAGEMENT OF CARE AREA TRANSITIONS OF INTRAVENOUS INFUSIONS

TECHNICAL FIELD

The subject matter described herein relates to infusion devices and uses thereof in a treatment setting, such as for example a hospital. In particular, the current subject matter is directed to management of infusions of drugs, fluids, and the like as a patient is transitioned between different care areas within the treatment setting.

BACKGROUND

Patient care in hospitals and other treatment settings can include active monitoring of various physiological parameters of a patient, especially with regard to infusion of various types of fluids delivered by one or more infusion devices.

Dose error reduction software (DERS) can be used with infusion devices (e.g. an infusion pump systems) for delivery of drugs, fluids, and other therapeutic substances (hereinafter referred to generally as "drugs"). A general goal of DERS is improvement in the safety and clinical utility of infusing intravenous drugs and fluids. A typical DERS system may be configured to allow creation of customized care areas. As used herein, the term "care area" can refer to a physical location or multiple locations within a hospital or other clinical care setting (hereinafter referred to generically as a "hospital"). For example, a care area can be defined as a neonatal intensive care unit (NICU), an intensive care unit, a trauma ward, etc., and such designations can be tied to physical locations (e.g. constrained within a specific location or locations within the hospital), or more generally to refer to a general class of patient, such as for example adult medical/surgical. Within a care area, one or more settings, such as for example custom device configurations, minimum and maximum hard and or soft limits per drug or fluid to be delivered, and the like may be established for an infusion device.

SUMMARY

In one aspect, a method includes transitioning an infusion device providing an in-progress infusion of at least one of a drug or a fluid consistent with one or more parameters of a first care area in a hospital to a second care area of the hospital, comparing details of the in-progress infusion against one or more second parameters defined for the second care area, making a compatibility determination between the in-progress infusion and the one or more second parameters defined for the seconds care area, selecting a handling mode of the in-progress infusion in the second care area based on the compatibility determination, and resolving the in-progress infusion consistent with the selected handling mode.

In optional variations, one or more of the following additional features can be added in any feasible combination. The making of the compatibility determination can include identifying whether the in-progress infusion is a good match, a partial match, a bad match, or a blocked infusion in the second care area. The compatibility determination can include identifying that the infusion is the good match, the good match can include a match between a drug/fluid information and a usage context for the in-progress infusion and the one or more second parameters, and the handling mode can include transitioning the infusion device from a first profile for the first care area to a second profile for the second care area while the in-progress infusion is allowed to continue. Alternatively, the compatibility determination can include identifying that the infusion is the partial match, the partial match can include a match between a drug/fluid information and a usage context for the in-progress infusion and the one or more second parameters but one or more in-progress infusion parameters of the in-progress infusion falling outside of an allowable range specified in the one or more second parameters, and the handling mode can include allowing the transitioning of the infusion device from a first profile for the first care area to a second profile for the second care area to complete and for the in-progress infusion to continue under its current one or more in-progress infusion parameters. In another alternative, the compatibility determination can include identifying that the infusion is the bad match, the bad match can include no match between the drug/fluid information and a usage context for the in-progress infusion and the one or more second parameters, and the handling mode can include allowing the in-progress infusion to complete in accordance with a first profile for the first care area before the transitioning of the infusion device to the second care area. In still another alternative, the compatibility determination can include identifying that the infusion is the blocked infusion, the blocked infusion can include the at least one drug or fluid being designated as non-transferable in the first care area, and the handling mode can include at least one of canceling the transitioning to the second care area and allowing completion of the transitioning while canceling the in-progress infusion.

Computer program products are also described that comprise non-transitory computer readable media storing instructions, which when executed one or more data processor of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection (wired or peer-to-peer wireless) between one or more of the computing systems, etc.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

One or more custom configurations and drug/fluid limits associated with the care areas in a hospital may, in some examples, be created using a DERS software application or module and then transferred to the various infusion devices or infusion systems including multiple infusion devices that are located in the hospital. An infusion system may include one or more infusion devices, such as for example single syringes, multichannel syringes, large volume parenteral (LVP) infusion pumps or other devices, patient-controlled analgesia (PCA) devices, or other infusion or enteral delivery systems or the like.

As part of the infusion setup process, the end user (for example a nurse) can be required to select an appropriate, current care area for a patient. As noted above, the care area can be based on one or more of a physical location (e.g. ICU, NICU, trauma, surgery, etc.), a patient type (e.g. adult medical/surgical), and the like depending on how the care areas are partitioned or otherwise defined within the hospital.

An issue that frequently arises with DERS systems in a hospital environment involves handling of ongoing infusions when a patient is transferred from a first care area to a second care area. One approach to dealing with infusions that are in process or otherwise ongoing when a patient is transferred from the first care area to the second care area is to force a shutdown of the infusion system. When the system is subsequently powered on, infusions consistent with one or more parameters or settings defined for the second care area can be selected by the end user (e.g. a nurse).

A hard shutdown approach as discussed in the preceding paragraph can be effective in assuring that each infusion occurring after transition to the second care area is consistent with parameters, settings, etc. that are appropriate for the second care area. However, a hard shutdown and restart of infusions based on a new set of parameters, settings, etc. appropriate to the second care area can be very disruptive of the infusion process. Each infusion must be stopped, reprogrammed, and restarted, which can result in delay, additional clinician (e.g. nurse, other end user, etc.) time, and potential negative clinical consequences (for example for drugs for which an interruption in delivery of even a very brief duration can alter the pharmacological effect). Additionally, a drug or fluid infusion initiated in the first care area might not be available under the parameters established for the second care area to which the patient has been transitioned. If the clinically appropriate approach would be to continue to infuse a given drug or fluid according to the parameters of the first care area until the current dosing of that drug of fluid has completed, the end user would be required either to delay switching the patient from the first care areas to the second care area for all of the currently ongoing drug or fluid infusions for that patient, or to switch the care area to the second care area and continue delivery of the given drug or fluid independently of the DERS system. Neither of these options is desirable from a patient care and safety standpoint.

Another approach to dealing with infusions that are ongoing during transition of a patient from a first care area to a second care area would be to allow the care area change, but to allow all infusions to continue under the settings of the previous care area until completed. This approach can be appropriate for some drugs or fluids, but can also be very inappropriate or even dangerous for other drugs or fluids, for example if the parameters, library of drugs and fluids available, dosing limits, doing methods, or the like that are set for the second care area present a conflict with those of the first care area.

To address these and potentially other difficulties with currently available solutions, implementations of the current subject matter can provide capabilities that allow for hospital management, end users (e.g. clinicians, nurses, etc.) caring for a patient, etc. to seamlessly and safely transition a patient from a first care area to a second care area without requiring that one or more infusion devices providing drugs, fluids, etc. to the patient be power cycled, reprogrammed, etc.

Consistent with implementations of the current subject matter, ongoing infusions can be classified according to one or more algorithms or other criteria to allow continuation of an ongoing, in-progress infusion where appropriate, or to force discontinuation based on the hospital's best practices or other parameters.

Figure 1:
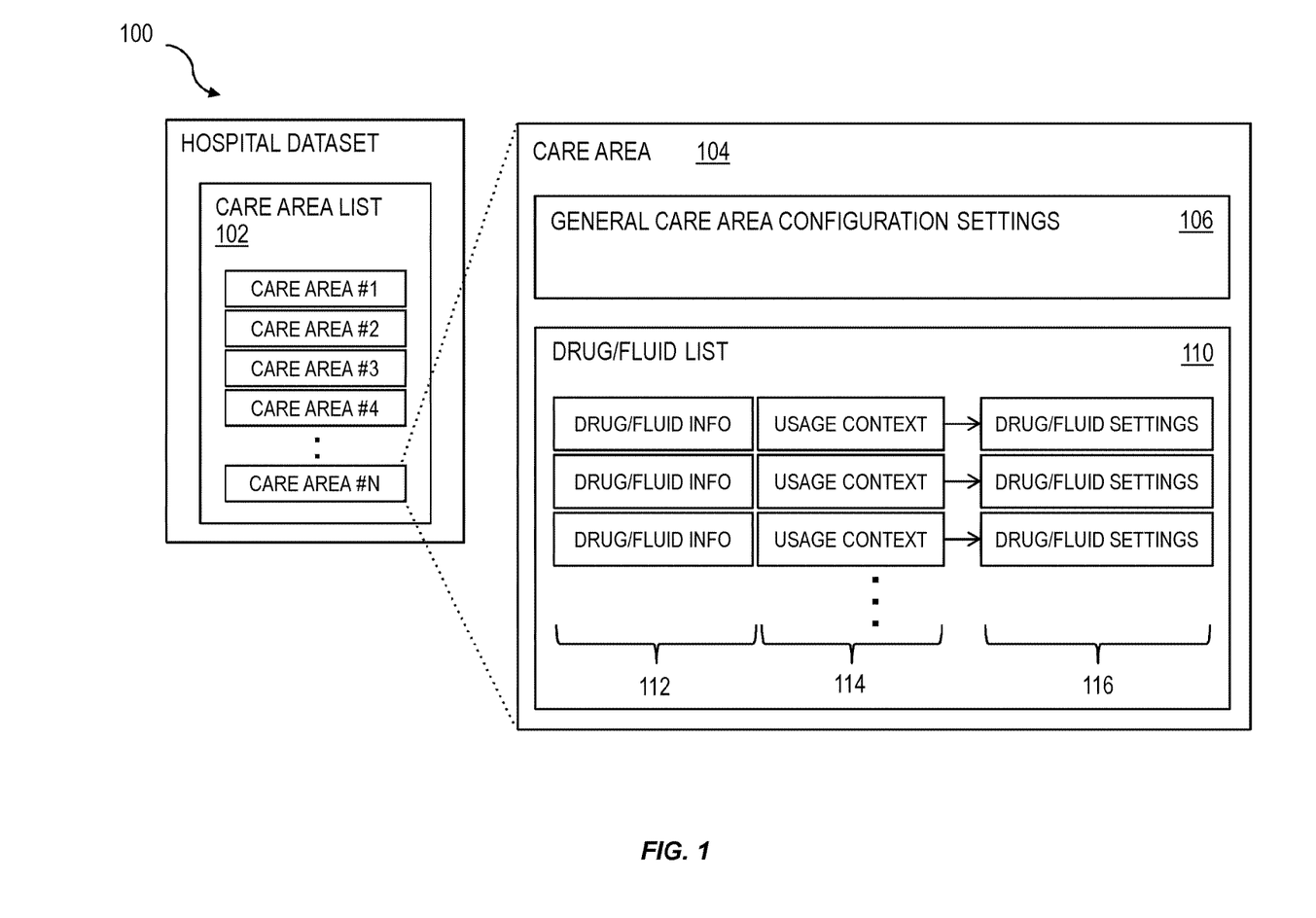
FIG. 1 shows a diagram illustrating a generalized representation of a hospital dataset.

In some implementations, a list of care areas can be contained in a hospital dataset, which can, for example, be stored in one or more data repositories accessible via one or more wired or wireless communication links with one or more infusion devices. Alternatively, a hospital dataset can be stored and updated at the individual infusion devices, for example by direct input via a user interface, by data transfer from a connected storage device, or the like. FIG. 1 shows a generalized representation of a hospital dataset 100 that includes a list 102 of care areas. Each care area 104 included in the list 102 contains general (non-drug/fluid specific) care-area-specific configuration settings 106 and a list of drugs/fluid-specific settings 110.

The general care-area-specific configuration settings 106 can apply to all infusions administered in that care area, and are not specific to a particular drug or fluid. Typical examples of general care-area-specific configuration settings 106 can include an air-in-line limit (e.g. a maximum allowable air bubble size) or an occlusion pressure limit (e.g. a maximum allowable line pressure).

As shown in FIG. 1, each drug/fluid entry in the list of drugs/fluid-specific settings 110 can include several types of information. The drug/fluid information 112 contains information that unambiguously establishes the drug or fluid and its form. Examples of this type of information include the drug or fluid name and concentration (if applicable). A usage context 114 contains information that defines the particular clinical context for the use of this drug or fluid. Examples of this type of information can include therapy/indication, infusion device type (LVP, syringe . . . ), or the like. Together, the drug/fluid information 112 and usage context 114 establish a clinical context for applying DERS limits and settings for delivery of that specific drug in a given care area. These limits and settings are contained in a drug/fluid settings entry 116 for each drug or fluid as shown in FIG. 1.

When an end user programs an infusion to be performed by an infusion device, the end user can be required (for example by a user interface of or associated with the infusion device) to enter or select the necessary information to identify the correct drug/fluid information and usage context for the infusion to be performed. One or more DERS limits to protect the programming session can be selected such that the correct drug-dependent settings are applied when the infusion starts.

Subsequent to initial programming of an infusion device, during which settings and limits from a first care area in which the infusion device is being operated are applied, implementations of the current subject matter enable a seamless transition of the infusion device, and the patient receiving an infusion from the infusion device, from a first care area to a second care area "on the fly." In other words, no restart of the system or interruption of ongoing infusions is necessary, except as mandated by the general care configuration settings 106 of the second care area to which the patient and the infusion device are being transitioned. Compatibility between a particular ongoing infusion and the parameters of the second care area can be determined, and based on this compatibility, (e.g. Good Match, Partial Match, Bad Match and Blocked, which are described in more detail below) the change in care area from the first care area to the second care area can be allowed or disallowed as appropriate. Optionally, if conflicts between an ongoing infusion and parameters of the second care area are detected, the end user can be notified of such conflicts, for example by a message shown on a display screen that presents a user interface, by activation of a visual or audio alarm, or the like.

As noted above, in reference to FIG. 1, care areas within a hospital can include care-area specific general care area configuration settings 106 as well as a list 110 of available drugs, fluids, etc. that can be delivered to patients within that care area subject to parameters specified for that care area 104, for example in a hospital dataset 100. These parameters can optionally include one or more of the following features. Within a specific care area, optionally within one or more care areas or even within each care area within the hospital, certain drugs or fluids can be designated as "non-transferable," indicating that they are not to be used in any other care area. An end user is able to select or change a care area to which the infusion device and associated patient are to be transitioned based on the care areas available in the hospital dataset 100. A user interface can be provided to allow the user to initiate a change in care area (e.g. from a first, current care area to a second, different care area) at any time.

When an infusion device (and its associated patient) is transitioned from a first care area to a second care area, implementations of the current subject matter can detect conflicts between an active infusion and one or more of the following parameters that can be defined as part of the general care area configuration settings 106 or the entries in the drug/fluid list 110 of the second care area: restricted use (e.g. the drug or fluid is not transferrable to the second care area), drug/fluid information and usage context match, DERS limits, dose limits, rate limits, care area configuration limits and settings, and the like.

Based on any differences between these parameters for the first care area and the second care area, a response can be generated for a given ongoing (e.g. in-progress during the transition from the first care area to the second care area) infusion that reflects a good match, a partial match, a bad match, a blocked infusion, etc.

An ongoing infusion being transferred from a first care area can be considered a good match with the second care area if a match for the infusion's drug/fluid information 112 and usage context 114 is found in the parameters defined for the second care area and if all infusion parameters fall within the allowable range specified for the second care area, both according to the general care area-specific configuration settings 106 and the entry for the specific drug or fluid in the drug/fluid list 110 specific for the second care area.

If a good match infusion is indicated or otherwise determined, the infusion device can be immediately transitioned from the profile for the first care area to a new profile for the second care area and can also immediately apply all configuration settings (e.g. both general and drug/fluid-specific) from the second care area. The end user can repeat (e.g. recall the original programming parameters) for this infusion when it completes, or resume (recall the latest running infusion parameters) if it was interrupted.

An ongoing infusion being transferred from a first care area can considered a partial match with the second care area if a match for the ongoing infusion's drug/fluid information and usage context is found in the parameters defined for the second care area but one or more parameters of the ongoing infusion fall outside the allowable range specified for the second care area, either from the general care area configuration settings 106 or the specific drug/fluid settings 116 for the second care area.

If a partial match infusion is indicated or otherwise determined, the infusion device can complete the transition from the first care area to the second care area. The end user can be notified (e.g. via a user interface or other communication approaches) that the DERS limits are being violated. While the infusion is running, the end user is allowed to modify the infusion parameters, and such modifications are validated against the limits defined in the second care area. The end user can be allowed to repeat or resume this infusion. However all parameters that violate limits in the second care area can be required to be brought into compliance.

An ongoing infusion being transferred from a first care area can be considered a bad match with the second care area if no match for the infusion's drug/fluid information 112 and usage context 114 is found in the parameters defined for the second are area.

If a bad match is indicated or otherwise determined, the infusion can be allowed to complete under the first care area. While the infusion is running, the end user can be permitted to modify the infusion parameters, which are validated against the limits defined for the first care area. The end user can repeat or resume this infusion. However all parameters that violate limits in the second care area can be required to be brought into compliance.

An ongoing infusion being transferred from a first care area can be blocked with respect to a second care area if drug or fluid has been designated as "non-transferable" in the first care area. If a blocked infusion is indicated or otherwise determined, the care area transition can be canceled for the infusion or for an entire infusion system that the infusion device is part of. Alternatively, the transition from the first care area to the second care area can be allowed but all blocked infusions can be permanently stopped. An end user can be prompted (e.g. via a user interface or the like) to decide which course of action to take. Alternatively, a default setting can be established such that the infusion system automatically selects one or the other approach in a predetermined manner (optionally with appropriate user notification).

Figure 2:
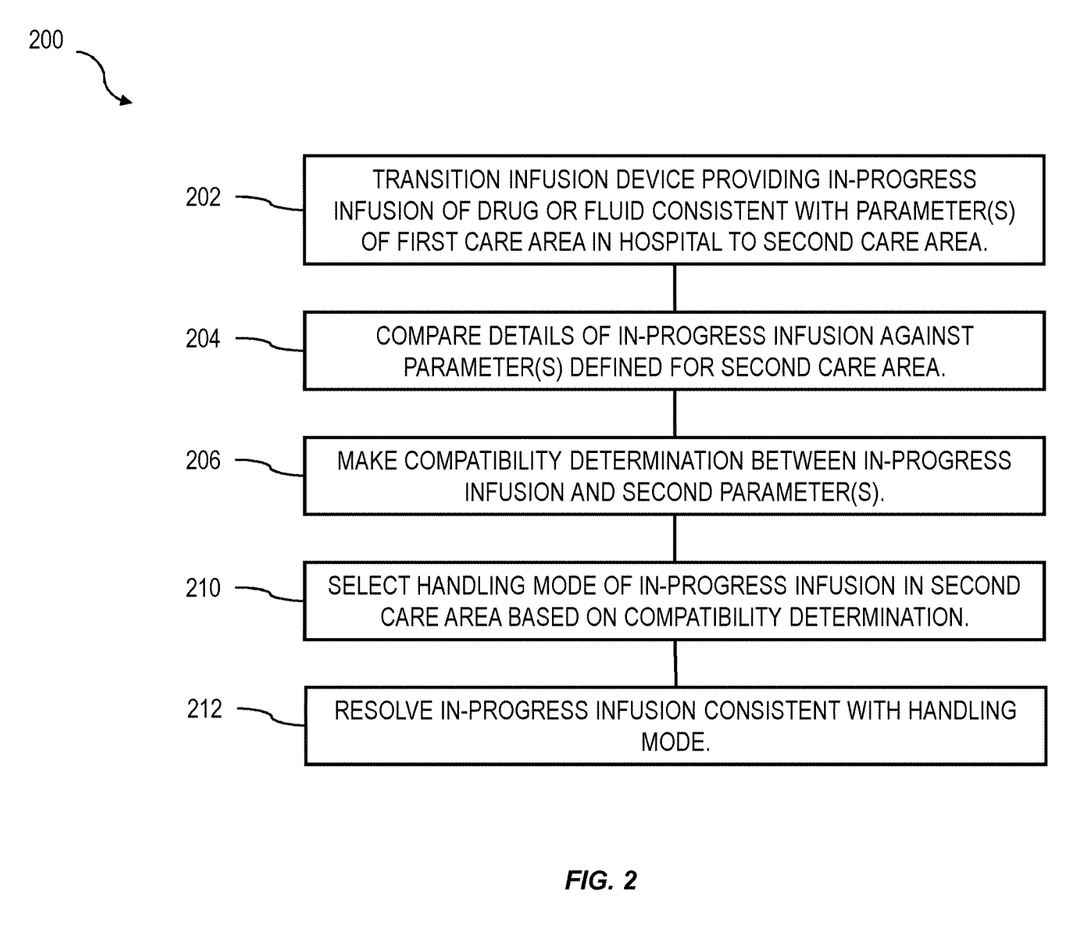
FIG. 2 shows a process flow diagram illustrating features of a method.

Consistent with one or more implementations of the current subject matter, FIG. 2 shows a process flow chart 200 illustrating features of a method. At 202, an infusion device providing an in-progress infusion of a drug or fluid consistent with parameters of a first care area in a hospital is transitioned to a second care area. Details of the in-progress infusion are compared at 204 against a set of parameters defined for the second care area. In some implementations of the current subject matter, the parameters defined for the second care area can include general care area-specific configuration settings 106 for the second care area and specific drug/fluid settings 116 for the second care area. A compatibility determination is made at 206 between the in-progress infusion and the parameters defined for the second care area, and at 210, a handling mode of the in-progress infusion in the second care area is selected based on the compatibility determination. At 212, the in-progress infusion is resolved consistent with the handling mode.

The handling mode can include one those described above, for example for a good match, partial match, bad match, or blocked compatibility determination as determined at 206. The resolving of the in-progress infusion can optionally occur by applying the operations specified in the handling mode.

Features of the current subject matter can be applicable for a system-wide care area change for a centrally controlled system of infusion channels, such as for example a central unit that provides power, a unified user interface for controlling one or more infusion channels (e.g. separate pumps or infusion device, etc.). Such a system can optionally include a monolithic single or multi-channel device, or a modular system of attachable and detachable infusion devices.

An alternative but related scenario occurs in the case of a modular infusion system where each infusion module has the ability to function independently, or may be attached to an aggregate system and function as an integrated part of it. In this situation, an implicit change in care area can occur when the module with its active infusion and care area is attached to the larger system, which has its own running infusions and care area. The described resolution process can be used to assimilate the new infusion into the aggregate system, with some modifications. In particular, the user choices for a blocked infusion might be to (1) remove the module or (2) to leave it and have the system stop the infusion.

One skilled in the art would recognize that the algorithms and approaches described above is just one example of how the system could manage care area changes. The system could readily support multiple algorithms. These algorithms could even be customizable by the institution to meet their specific patient care needs. It is also possible to find middle ground in the system response to bad or partial matches: some hybrid of the first care area settings and the second care area settings could be used, rather than the whole of one or the other.

The transitioning from the first care area to the second care area can be performed in response to a user input identifying to an infusion device or infusion system including an infusion device that the transition is occurring. Alternatively, in the case of a modular infusion device that can be removed from a first central system in the first care area, moved with a patient to a second care area, and reattached to a second central system in the second care area, the transition can occur through communication of the modular diffusion device with the second central system to indicate that the modular device is now in the second care area. In yet another alternative, one or more location indication devices, such as for example a global positioning system (GOS) signal or other locator beacon, a wireless location signal of some other kind, etc., can be received by the infusion device to indicate that the transition has occurred.

Features that can be included in various implementations of the current subject matter can be understood in reference to the following, non-limiting, example use cases.

In a first example, a pump (e.g. an infusion device) is configured in a "Medical/Surgical" care area, where it is attached to a patient and delivering the drug heparin at a concentration of 25,000 units per 250 mL in a "High Dose" therapy mode at 900 units/h. The maximum dose limit is 1000 unit/h. The patient is transferred from the "Medical/Surgical" care area to a second car area: the "ICU" care area. Upon arrival the ICU care area, the end user (e.g. a nurse or other clinician) switches the pump's current care area from "Medical/Surgical" to "ICU."

A scan of drugs and fluids assigned to a "ICU" care area profile finds an entry for heparin 25000 units/250 mL in the high dose therapy with dosing units of units/h (all the same as the parameters in the Medical/Surgical care area). The system does determine that the DERS limits for the entry in the "ICU" care area are more strict, in this case, 950 unit/h, but that the current infusion falls within the guidelines. The system determines that this entry is compatible with the current infusion (and is therefore a "good match") and so updates the infusion with the data from the "ICU" profile entry and successfully completes the switch to the "ICU" care area without further user action.

In a second example, a pump (e.g. an infusion device) is configured in a "Medical/Surgical" care area, where it is attached to a patient and delivering the drug heparin at a concentration of 25,000 units per 250 mL in a "High Dose" therapy mode at 900 units/h. The patient is transferred from the "Medical/Surgical" care area to an "ICU' Care Area. Upon arrival the ICU clinician switches the pump's current Care Area to 'ICU'.

A scan of drugs and fluids assigned to a "ICU" care area profile finds an entry for heparin 25,000 units per 250 mL in the high dose therapy with dosing units of units/h (all the same as the parameters in the Medical/Surgical care area). However, the system determines that the DERS limits for the entry in the "ICU" care area are more strict than those of the Medical/Surgical care area, in this case, 800 unit/h. As such, the current infusion falls outside these guidelines. The system determines that this entry is compatible with the current infusion (however, as only a partial match) and so updates the infusion with the data from the "ICU" entry and successfully completes the switch to the "ICU" care area without further user action required. Upon the transition from the first care area ("Medical/Surgical") to the second care area ("ICU"), the system allows the infusion to continue to operate with the current infusion parameters. Additional user action is not required. However the infusion is conspicuously identified by the system user interface as infusing outside the DERS limits for the ICU care area. The next time the infusion is accessed for programming, the end user is required to bring the infusion parameters into compliance with the ICU care area settings.

An infusion device can be part of an infusion system as noted above. Implementations of the current subject matter of the current subject matter are not restricted to any specific type of infusion devices or infusion systems.

Figure 3:
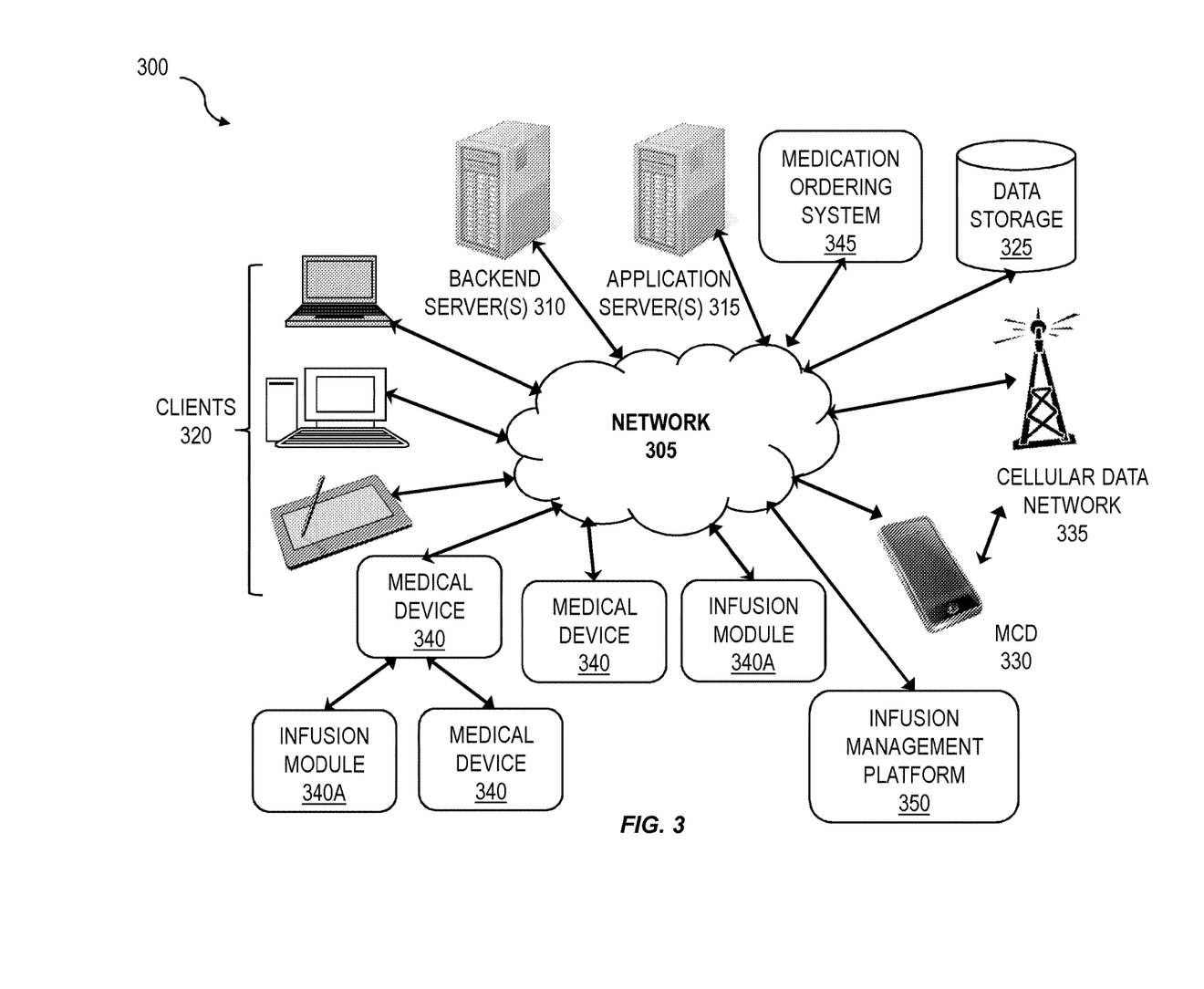
FIG. 3 shows a diagram illustrating a computing landscape including a modular medical device system.

FIG. 3 is a system diagram illustrating an example of a computing landscape 300 within a healthcare environment such as a hospital. Various devices and systems, both local to the healthcare environment and remote from the healthcare environment, can interact via at least one computing network 305. This computing network 305 can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

In particular, aspects of the computing landscape 300 can be implemented in a computing system that includes a back-end component (e.g., as a data server 310), or that includes a middleware component (e.g., an application server 315), or that includes a front-end component (e.g., a client computer 320 having a graphical user interface or a Web browser through which a user may interact with an implementation of the subject matter described herein), or any combination of such back-end, middleware, or front-end components. A client 320 and server 310, 315 are generally remote from each other and typically interact through the communications network 310. The relationship of the clients 320 and servers 310, 315 arises by virtue of computer programs running on the respective computers and having a client-server relationship to each other. Clients 320 can be any of a variety of computing platforms that include local applications for providing various functionality within the healthcare environment. Example clients 320 include, but are not limited to, desktop computers, laptop computers, tablets, and other computers with touch-screen interfaces. The local applications can be self-contained in that they do not require network connectivity and/or they can interact with one or more of the servers 310, 315 (e.g., a web browser).

A variety of applications can be executed on the various devices and systems within the computing landscape such as electronic health record applications, medical device monitoring, operation, and maintenance applications, scheduling applications, billing applications and the like.

The network 310 can be coupled to one or more data storage systems 325. The data storage systems 325 can include databases providing physical data storage within the healthcare environment or within a dedicated facility. In addition, or in the alternative, the data storage systems 325 can include cloud-based systems providing remote storage of data in, for example, a multi-tenant computing environment. The data storage systems 325 can also comprise non-transitory computer readable media.

Mobile communications devices (MCDs) 330 can also form part of the computing landscape 300. The MCDs 330 can communicate directly via the network 305 and/or they can communicate with the network 305 via an intermediate network such as a cellular data network. Various types of communication protocols can be used by the MCDs 330 including, for example, messaging protocols such as SMS and MMS.

Various types of medical devices 340 can be used as part of the computing landscape 300. For example, the landscape can include comprise various systems/units for delivering fluid (including medication) to a patient. On particular type of medical device 340 is an infusion module 340A, which is an example of an infusion device consistent with the description above. The infusion modules 340A can include various types of infusion pumps including peristaltic infusion pumps, large volume infusion pumps, and syringe pumps. The infusion modules 340A can be directly coupled to the network 305 and/or they can be coupled to a medical device 340 which is, in turn, coupled to the network 340.

The medical devices 340 can comprise, unless otherwise specified, any type of device or system with a communications interface that characterizes one or more physiological measurements of a patient and/or that characterize treatment of a patient. In some cases, the medical devices 340 communicate via peer to peer wired or wireless communications with another medical device 340 (as opposed to communicating with the network 305). For example, the medical device 340 can comprise a bedside vital signs monitor that is connected to other medical devices 340, namely a wireless pulse oximeter and to a wired blood pressure monitor. One or more operational parameters of the medical devices 340 can be locally controlled by a clinician, controlled via a clinician via the network 305, and/or they can be controlled by one or more of a server 315, 320, a client 325, a MCD 330, and/or another medical device 340. A medical device 340 including one or more infusion modules 340A is an example of an infusion system consistent with the descriptions above.

The computing landscape 300 can provide various types of functionality as may be required within a healthcare environment such as a hospital. For the medical devices 340 can provide data characterizing one or more physiological measurements of a patient and/or treatment of a patient (e.g., medical device 340 can be an infusion management system, etc.). The data generated by the medical devices 340 can be communicated to other medical devices 340, the servers 310, 320, the clients 320, the MCDs 330, and/or stored in the data storage systems 325.

The computing landscape 300 can also include at least one medication ordering system 345. The medication ordering system 345 is coupled to the network and enables orders (e.g., prescriptions, etc.) to be generated and monitored. The medication order system 345 can be accessed, for example, via the one of the clients 320 and MCDs 330 via the application server 315. The medication ordering system 345 can specify a plurality of medications and/or other fluids to be infused into a patient over a pre-defined period of time and according to a pre-defined sequence via at least one infusion module 340A. This orders can be stored in the data storage 325 and/or pushed out to other clients 320, an MCD 330, and/or one or more of the medical devices 340. In some cases, caregivers alter the timing and sequence of such medication delivery based on reactions from the patient (as measured by various physiological sensors, etc.).

One more of the medical devices 340 (such as infusion modules 340A) can monitor an amount of fluid (e.g., medication, etc.) delivered to a patient. Fluids delivered to patients are referred to herein as infusions. Unless otherwise specified, references herein to medications should also be construed to include non-medication fluids (e.g., blood, saline, etc.) for delivery to a patient via an infusion module 340A.

As noted above, containers housing fluids such as medication often vary from the volumes ordered by a pharmacist/clinician. A software-implemented infusion management platform 350 can be provided that includes a graphical user interface for tracking and monitoring infusions for one or more patients. The infusion management platform 350 communicates with the infusion modules 340A via the network 305. The infusion modules 340A can directly or indirectly provide various attributes relating to a particular infusion to the infusion management platform 350 (e.g., patient identifier, medication container identifier, medication type, rate of medication administration, infusion module identifier, etc.). Such attributes can be provided, for example, via messages sent from the infusion modules 340A. In some cases, the infusion management platform 350 receives medication orders from the medication ordering system 345 and then associates such orders with particular infusion modules 340A and/or particular patients (who are later associated with the infusion modules 340A).

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A method of infusing at least one drug or fluid to a patient comprising:
   initiating an infusion of at least a first drug and a second drug to a patient by an infusion device, the infusion device comprising at least one programmable processor and memory storing instructions for execution by the at least one programmable processor;
   determining, by the infusion device, that the infusion device is to be physically moved from a first care area to a second care area;
   comparing the first drug and the second drug to a list of drugs that are allowed to be infused in the second care area;
   determining, based on the comparison, that the second drug is not allowed to be used in the second care area; and stopping the infusion of the second drug while allowing infusion of the first drug;

activating an alarm to notify an end user that the second drug is not transferrable to the second care area.

2. The method of claim 1, wherein the drug parameter further includes information that unambiguously establishes the drug and a form of the at least one drug.

3. The method of claim 1, further comprising accessing a list of care settings for a hospital in which the infusion device is located, the list of care setting including the first drug parameter and the second drug parameter.

4. The method of claim 1, wherein comparing the first drug parameter of the first care setting to a second drug parameter of the second care setting is initiated in response to the infusion device physically moving from the first care setting to the second care setting.

5. The method of claim 1, further comprising determining that the infusion device is physically moving from the second care setting in the hospital to a third care setting in the hospital; and comparing the second drug parameter of the second care setting to a third drug parameter of the third care setting.

* * * * *